United States Patent [19]
Grollier

[11] Patent Number: 5,874,091
[45] Date of Patent: Feb. 23, 1999

[54] COSMETIC COMPOSITION COMPRISING A DISPERSION OF LIPID VESICLES AS WELL AS MELANIN PIGMENTS

[75] Inventor: Jean-François Grollier, Paris, France

[73] Assignee: L'Oreal, Paris, France

[21] Appl. No.: 271,990

[22] Filed: Jul. 8, 1994

Related U.S. Application Data

[63] Continuation of Ser. No. 859,377, May 27, 1992, abandoned.

[30] Foreign Application Priority Data

Sep. 27, 1990 [LU] Luxembourg ............................... 87 814

[51] Int. Cl.$^6$ ..................................................... A61K 7/00
[52] U.S. Cl. ................................. 424/401; 8/405; 8/407; 424/59; 424/70.9; 424/450
[58] Field of Search ............................... 8/409, 405, 423; 424/59, 63, 70.9, 78.02, 78.03, 450

[56] References Cited

U.S. PATENT DOCUMENTS

| | | | |
|---|---|---|---|
| 4,776,857 | 10/1988 | Carroll et al. | 8/423 |
| 4,822,375 | 4/1989 | Lang et al. | 8/423 |
| 4,855,144 | 8/1989 | Leong et al. | 424/487 |
| 4,961,754 | 10/1990 | Grollier | 8/423 |
| 4,968,497 | 11/1990 | Wolfram et al. | 424/59 |
| 5,006,331 | 4/1991 | Gaskin | 424/70.1 |
| 5,021,200 | 6/1991 | Vanlerberghe et al. | 264/4.3 |
| 5,073,174 | 12/1991 | Vayssie et al. | 8/406 |
| 5,112,360 | 5/1992 | Garoche et al. | 8/406 |
| 5,124,081 | 6/1992 | Vanlerberghe et al. | 424/450 |
| 5,188,844 | 2/1993 | Ahene et al. | 424/574 |
| 5,205,837 | 4/1993 | Andrean et al. | 8/405 |
| 5,210,076 | 5/1993 | Berliner et al. | 514/21 |
| 5,240,715 | 8/1993 | Ahene et al. | 424/574 |
| 5,244,497 | 9/1993 | Junino et al. | 106/498 |
| 5,256,403 | 10/1993 | Gaskin | 424/59 |
| 5,316,774 | 5/1994 | Eury et al. | 424/501 |
| 5,346,509 | 9/1994 | Schultz et al. | 8/423 |

FOREIGN PATENT DOCUMENTS

| | | |
|---|---|---|
| 0313380 | 4/1989 | European Pat. Off. . |
| 0379409 | 7/1990 | European Pat. Off. . |
| 0386680 | 9/1990 | European Pat. Off. . |
| 2207153 | 1/1989 | United Kingdom . |

*Primary Examiner*—Robert H. Harrison
*Attorney, Agent, or Firm*—Nixon & Vanderhye, P.C.

[57] ABSTRACT

This composition based on lipid vesicles dispersed in an outer phase is characterized in that it contains at least one melanin pigment in the aqueous outer phase. The melanin pigments may be carried on mineral or polymeric fine particulate or lamellar fillers. The composition obtained can be used in the field of cosmetics where it makes it possible to obtain a highly homogeneous dispersion of the melanin pigment that can be distributed evenly over the skin or hair; it increases the period of protection of keratinous substances against the harmful effects of ultraviolet radiation; it promotes tanning of the skin and gives it an even color and better appearance; it colors grey hair; and it causes improved storage of the melanin pigment in the stratum corneum.

29 Claims, No Drawings

COSMETIC COMPOSITION COMPRISING A DISPERSION OF LIPID VESICLES AS WELL AS MELANIN PIGMENTS

This is a continuation of application Ser. No. 07/859,377, filed May 27, 1992, abandoned.

The present invention relates to a cosmetic composition based on lipid vesicles, said composition including melanin pigments, as well as to the use thereof, especially for the protection of keratinous substances, in particular the skin and hair, against ultraviolet radiation, and for pigmentation of the skin and hair in order especially to color them in a color similar to that of the natural pigmentation.

Compositions based on lipid vesicles are already known, especially in the above-mentioned field. Lipid vesicles, which are generally in the form of aqueous dispersions, are characterized by a lamellar structure of layers consisting of at least one lipid double layer, and encapsulating an aqueous phase which may include water-soluble active substances, which are thus protected from external conditions.

The vesicles can be obtained from ionic lipids and/or non-ionic lipids: the term "vesicle" used in the present application encompasses all cases.

The natural protection of the human skin against ultraviolet radiation depends on the quantity of melanin pigment present in the melanocytes, and this level varies according to the different types of skin, from fair to dark. This photoprotective role of melanin is well known. Thus it is that in individuals having a skin of type I, II or III, which does not produce melanin in sufficient quantity, prolonged exposure to the sun may cause premature aging of the skin and skin cancers.

To reduce the lack of this pigment in the epidermis, it has already been proposed to apply melanin to the skin. However, topical application of melanin poses problems at the level of using it in compositions, on account of the difficulty of dispersion and poor compatibility in the carriers used in cosmetics. The complexity of these problems therefore limits its use.

Moreover, still in order to reduce the lack of this pigment in the epidermis, it has also been proposed, according to French patent applications FR-A-2 623 716 and FR-A-2 624 374, to use, in sun or tan compositions, melanin precursors such as L-tyrosine or water-soluble derivatives of L-tyrosine, which, on crossing the skin barrier, are transformed into metabolizable L-tyrosine and lead to the formation of melanin in human skin. The above-mentioned patent applications thus propose compositions based on hydrated lipid lamellar phases or liposomes containing tyrosine or a tyrosine derivative. The efficacy of such compositions is nevertheless limited on account of the use of a melanin pigment precursor. In EP-A-0 386 680 is described a method for tanning the skin which consists of applying to the skin a composition containing a certain quantity of melanin complexed with liposomes, the melanin being either in the lipid walls of the liposomes, or in the encapsulated aqueous phase.

According to the invention, it has now surprisingly been discovered that a composition in the form of a dispersion of ionic and/or non-ionic amphiphilic lipid vesicles, containing in the outer phase at least one melanin pigment already formed, made it possible to remedy the problems encountered up to now, forming an advantageous cosmetic composition under several aspects:

it makes it possible to obtain a very homogeneous dispersion of the melanin pigment which can thus be distributed evenly over the skin or hair;

it makes it possible to obtain a stable composition particularly under UV irradiation; in particular it was observed that there is no peroxidation and therefore no rancidification of fatty substances;

it increases the period of protection of keratinous substances against the harmful effects of ultraviolet radiation and makes it possible to potentialize the protective effect;

it promotes tanning of the skin and gives it an even color and better appearance;

it colors grey hair; and it causes improved storage of the melanin pigment in the stratum corneum.

The present invention therefore relates to a cosmetic composition comprising, in an aqueous dispersion, lipid vesicles with a lamellar structure encapsulating an aqueous phase, characterized in that it contains at least one melanin pigment, having a particle size between about 500 nm and 50,000 nm, mixed with the vesicles in the outer phase of the dispersion. A portion of this melanin pigment may if occasion arises be present in the encapsulated phase of the vesicles.

The melanin pigment or pigments can be obtained (A) by oxidation of at least one indole compound, (B) by oxidant or enzymatic polymerization of melanin precursors, or (C) by extraction of melanin from substances containing it.

(A) The melanin pigments can firstly be obtained by oxidation of at least one indole compound selected in particular from among those satisfying the formula (I):

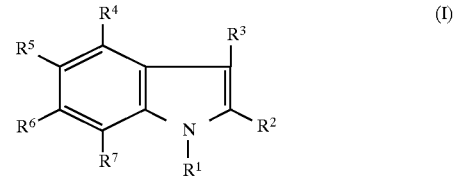

where:

$R^1$ and $R^3$ denote, independently of each other, hydrogen or $C_1-C_4$ alkyl;

$R^2$ denotes hydrogen, $C_1-C_4$ alkyl, carboxyl or $(C_1-C_4$ alkoxy)-carbonyl;

$R^4$ and $R^7$ denote, independently of each other, hydrogen, hydroxy, $C_1-C_4$ alkyl, amino, $C_1-C_4$ alkoxy, $(C_2-C_4$ acyl)-oxy, $(C_2-C_4$ acyl)-amino;

$R^5$ denotes hydrogen, hydroxy, $C_1-C_4$ alkoxy, $C_1-C_4$ alkyl, halogen, amino, $(C_2-C_{14}$ acyl)-oxy, $(C_2-C_4$ acyl)-amino, trimethylsilyloxy;

$R^6$ denotes hydrogen, hydroxy, $C_1-C_4$ alkoxy, amino, $(C_2-C_4$ acyl)-oxy, $(C_2-C_4$ acyl)-amino, trimethylsilyloxy, $(C_2-C_4$ hydroxyalkyl)-amino;

$R^5$ and $R^6$ may also form, together with the carbon atoms to which they are attached, a methylenedioxy ring which may be substituted by a $C_1-C_4$ alkyl or $C_1-C_4$ alkoxy group, or a carbonyldioxy ring:

at least one of the radicals $R^4$ to $R^7$ denotes an OZ or $NHR^0$ group with not more than one of the radicals $R^4$ to $R^7$ denoting $NHR^0$; and not more than two of the radicals $R^4$ to $R^7$ denote OZ and, in the event that Z denotes hydrogen, the two OH are in positions 5 and 6; and at least one of the radicals $R^4$ to $R^7$ denotes hydrogen, and in the event that only one of these radicals denotes hydrogen, only one radical from among $R^4$ to $R^7$ then denotes $NHR^0$ or OZ, the other radicals denoting $C_1-C_4$ alkyl;

the $R^0$ of the $NHR^0$ group denoting hydrogen, $C_2$–$C_4$ acyl, $C_2$–$C_4$ hydroxyalkyl, and the Z of the OZ group denoting hydrogen, $C_2$–$C_{14}$ acyl, $C_1$–$C_4$ alkyl, or trimethylsilyl, and alkali metal, alkaline earth metal, ammonium or amine salts thereof.

These indole compounds are preferably selected from among 4-hydroxyindole, 5-hydroxyindole, 6-hydroxyindole, 7-hydroxyindole, 4-hydroxy-5-methoxyindole, 4-hydroxy-5-ethoxyindole, 2-carboxyl-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole,3-methyl-5,6-dihydroxyindole, 2,3-dimethyl-5,6-dihydroxyindole,2-carboxyl-5,6-dihydroxyindole, 4-hydroxy-5-methylindole, 2-carboxyl-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, indole, 5-hydroxy-3-methylindole, 5-acetoxy-6-hydroxyindole, 5-hydroxy-2-ethoxycarbonylindole, 6-hydroxy-2-carboxyl-5-methylindole, 6-hydroxy-2-ethoxycarbonyl-5-methoxyindole, 6-N-B-hydroxyethylaminoindole, 4-aminoindole, 5-aminoindole, 6-aminoindole, 7-aminoindole, N-methyl-6β-hydroxyethylaminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-dimethoxyindole, 5,6-methylenedioxyindole, 5,6-trimethylsilyloxyindole, 5,6-dihydroxyindole phosphoric ester and 5,6-dibenzyloxyindole, and addition salts of these compounds.

5,6-dihydroxyindole and 6-hydroxyindole are particularly preferred.

Oxidation of the indole compound of formula (I) can be carried out in an aqueous medium or water/solvent(s), in air, in the presence or absence of an alkaline agent and/or a metallic oxidation catalyst such as for example copper ion.

The reaction medium preferably consists of water and may if occasion arises consist of a mixture of water and at least one solvent selected in such a way that it will rapidly solubilize the indole compound of formula (I). Among these solvents we might mention, as examples, lower $C_1$–$C_4$ alcohols such as ethyl alcohol or propyl or isopropyl alcohol, tert-butyl alcohol, alkylene glycols such as ethylene glycol, propylene glycol, alkylene glycol alkyl ethers such as monomethyl, monoethyl and monobutyl ethers of ethylene glycol, monomethylethers of propylene glycol and of dipropylene glycol, and methyl lactate.

Oxidation can also be carried out by using hydrogen peroxide in the presence of an alkaline agent such as preferably ammonia, or in the presence of an iodide ion, the iodide being preferably the iodide of an alkali metal, alkaline earth metal or ammonium.

Oxidation can also be carried out by using periodic acid and water-soluble salts and derivatives thereof, permanganates and bichromates such as those of sodium or potassium, sodium hypochlorite, potassium ferricyanide, ammonium persulphate, silver oxide, lead oxide, ferric chloride, sodium nitrite, salts of rear earths including particularly cerium, and organic oxidants selected from among ortho- and parabenzoquinones, ortho- and parabenzoquinone mono- or diimines, 1,2- and 1,4-naphthoquinones, 1,2- and 1,4-naphthoquinone mono- or diimines as defined in application EP-A-O 376 776. The preferred periodic acid salt is sodium periodate.

It is possible to activate the oxidizing agents with a pH modifier.

Enzymatic oxidation may also be envisaged.

The insoluble product is isolated by filtration, centrifugation, lyophilization or atomization; it is then ground or micronized to obtain the desired granulometry.

(B) The melanin pigments according to the invention may also be derived from oxidant or enzymatic polymerization of melanin precursors such as L-tyrosine, L-dopa, catechol and derivatives thereof.

(C) The melanin pigments according to the invention may finally be derived from extraction of melanin from substances such as human hair, ink of cephalopods (cuttlefish, octopuses) also known by the name of sepiomelanin, in which case the pigment is ground and purified before using it.

Preferably the pigments mentioned in paragraph (A) obtained by oxidation of at least one indole compound and in paragraph (C) obtained by extraction of melanin from substances containing it are used.

According to one particular embodiment of the invention, the melanin pigment or pigments are combined with at least one particulate filler to form a composite melanin pigment. In this case, the melanin pigment or pigments may result from the oxidation of at least one indole compound of formula (I), as defined above, mixed with the filler, in an essentially non-solvent medium of said filler, at a temperature which may be from ambient temperature to about 100° C., or from oxidant polymerization of melanin precursors on the filler.

The general conditions of oxidation of the indole compounds of formula (I) are the same as those mentioned above.

According to a first embodiment, the particulate filler is an inert mineral filler with a granulometry less than 20,000 nm, particularly less than 10,000 nm and close to 5,000 nm, advantageously consisting of calcium carbonate, silica or titanium oxide particles. Such composite melanin pigments deposited on a mineral filler are described, as well as the preparation thereof, in French patent application FR-A-2 618 069.

According to a second embodiment of the present invention, the particulate filler is an inert polymeric filler with a granulometry less than 100,000 nm, particularly from 10 to 50,000 nm, advantageously selected from among natural or synthetic, organic or inorganic, crosslinked, crystalline or amorphous polymers, having a molecular weight between 5,000 and 5,000,000. Composite melanin pigments on a polymeric filler as well as the preparation thereof are described in Luxemburg patent application LU-A-87 429.

The organic or synthetic polymers are in particular selected from among polymers derived from keratin, chitin or cellulose, or from among polyamides or homopolymers or copolymers resulting from the polymerization of monoethylenic or polyethylenic, aliphatic or aromatic, crosslinked, crystalline or amorphous monomers.

The polymers derived from keratin are selected from among animal or human keratins. Other polymers derived from keratin that can be used are chemically modified keratins having a molecular weight between 10,000 and 250,000 and, in particular, partially hydrolyzed keratin (or keratin hydrolysate) having a molecular weight between 50,000 and 200,000; this hydrolyzate is preferably obtained by moderated alkaline hydrolysis; products of this type are for example sold under the name of "KERASOL" by the company "CRODA." Other modified keratins are sulphonic keratins with a molecular weight between 10,000 and 100, 000 obtained by oxidation of all or some of the disulphide bonds of the cystine groups of the keratin into cysteic acid groups. We might also mention, as a keratin derivative, silk fibroin.

The polymers derived from chitin include first of all chitin, which is a natural polymer, and the deacetylated chitin derivative known by the name of chitosan, obtained by saponification of the acetyl groups of chitin. Chitosan as proposed in the trade is partially acetylated and contains 70–90% by weight of chitosan. It can also be used in the form of insoluble salts such as sulphates and phosphates. Products of this type are sold for example under the name of "KYTEX" by the company "HERCULES."

The cellulosic polymers are selected more particularly from among microcrystalline celluloses such as the products sold under the name of "AVICEL" by the company "FMC CORPORATION."

Among the synthetic polymers, we might mention more particularly polyethylene, polypropylene, polystyrene, poly (methyl methacrylate) sold under the names "MICROPE-ARL M" and "MICROPEARL M100" by the company "SEPPIC.," and crosslinked poly(methyl methacrylate) such as the product sold under the name of "MICROPEARL M 305" by the company "SEPPIC." Other polymers are in particular selected from among crosslinked poly-β-alanine as described in French patent 2 530 250 or advantageously presented in the form of microspheres having a very low dispersity of size, 85% by weight having a granulometry between 28,000 and 46,000 nm, the crosslinking level of which is between 1 and 15% and preferably between 1 and 8%.

One can also use, as polymers, products known by the name of microsponges such as crosslinked polymers of styrene/divinylbenzene or methyl methacrylate/ethylene glycol dimethacrylate or vinyl stearate/divinylbenzene, as described in patents WO-88/01164 and U.S. Pat. No. 4,690, 825. Such polymers essentially consist of crosslinked polymer beads comprising an inner network of pores, capable of retaining the melanin pigment. Other polymers of this type are hollow microspheres of a copolymer of vinylidene chloride and acrylonitrile, sold under the name of "EXPAN-CEL" by the company "KEMA NORD;" or else porous microspheres of polyamide 12, polyamide 6 or copolyamide 6/12, sold under the name of "ORGASOL" by the company "ATOCHEM;" these microspheres preferably have a granulometry between 10,000 and 50,000 nm.

One can also use silicone powders which are rubbers, resins and more particularly organopolysiloxane elastomers.

According to a third embodiment, the particulate filler is a filler consisting of organic or mineral particles with a lamellar structure having a size less than 50,000 nm.

The particles of lamellar structure, consisting of layers for which the ratio between the largest dimension and the thickness is particularly between 2 and 100, are selected in particular from among the following products: L-lauroyllysine such as the product sold under the name of "AMIHOPE L.L." by the company "AJINOMOTO;" ceramic microparticles which may be coated with zirconium powder such as the products sold under the names of "TORAYCERAM ZP 550" and "ZP 40001" by the company "TORAY;" lamellar titanium dioxide such as the products sold under the names of "LUXELEN SILK D" and "LUX-ELEN SS" by the company "SUMITOMO," lamellar talc, boron nitride such as the products sold respectively under the names "Boron nitride SF" or "SHP" by the companies "WACKER" and "KAWASAKI;" lamellar mica such as the product sold under the name of "MICA CONCORD 1000"

by the company "SCIAMA;" bismuth oxychloride such as the product sold under the name of "PEARL GLO" by the company "MALLINCKRODT." The size of the particles of lamellar structure used according to the invention is preferably less than 50,000 nm and in particular less than 25,000 nm; their size is generally greater than 500 nm; it is in particular between 1,000 and 20,000 nm. These particles have a thickness generally greater than 10 nm. These lamellar particles may be in the form of a stratified structure. Details and further particulars concerning the structure and preparation of these melanin pigments on lamellar fillers are described in patent application FR-90-090 053 filed on the 16th Jul. 1990 in the name of the applicant.

Vesicles of the compositions according to the invention are prepared from a lipid phase comprising at least one ionic amphiphilic lipid and/or a non-ionic amphiphilic lipid which may be combined with at least one stabilising additive, said vesicles containing an encapsulated aqueous phase which may contain cosmetically active products such as moisturising agents or soothing agents.

Among the non-ionic amphiphilic lipids that can be used, we might mention (1) linear or branched polyglycerol ethers of the formula:

where:
—$C_3H_5(OH)O$ is represented by the following structures taken in combination or separately:

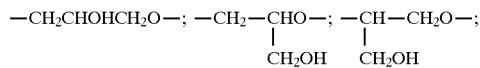

$\bar{n}$ is a mean statistical value between 2 and 6;
$R^{10}$ denotes:
  a) an aliphatic, linear or branched chain containing 12 to 18 carbon atoms;
  b) an $R^{11}CO$ radical, where $R^{11}$ is an aliphatic, linear or branched, $C_{11}$–$C_{17}$ radical;
  c) an $R^{12}$—[—$OC_2H_3(R^{13})$—]— radical, where:
    $R^{12}$ may assume the meaning (a) or (b) given for $R^{10}$;
    $OC_2H_3(R^{13})$— is represented by the following structures, taken in combination or separately:

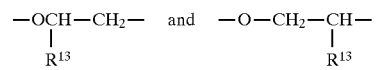

where $R^{13}$ assumes the meaning (a) given for $R^{10}$;

(2) polyoxyethylenated fatty alcohols, polyoxyethylenated sterols;
(3) polyhydric alcohol esters which may be polyoxyethylenated;
(4) cerebrosides; and
(5) oxyethylenated polyglycerol stearate.

Among the ionic amphiphilic lipids that can be used, we might mention:
phosphoaminolipids;
glycolipids;
natural phospholipids such as egg or soy lecithin, sphingomyelin, phosphatidyl serine, dipalmitoyl phosphatidyl choline and hydrogenated lecithins.

Preferably the above non-ionic amphiphilic lipids and in particular the polyglycerol ethers of formula (II) are used.

The stabilizing additive is intended, in a known manner, to modify the permeability and/or the surface charge of the vesicles. It is preferably selected from the group composed of sterols and anionic stabilizers. The sterol is advantageously cholesterol. The anionic stabilizer is advantageously selected on the one hand from among monosodium or disodium salts of ($C_{14}$–$C_{22}$ acyl) glutamates such as the monosodium salt of N-stearoyl-glutamic acid, disodium salts with acyl radicals of copra and suet or else cocoyl and stearoyl radicals, and on the other hand from among phosphoric esters of $C_{12}$–$C_{22}$ fatty alcohols. In a known manner, both a sterol and an anionic stabilizer can be added to the amphiphilic lipid(s).

The vesicles advantageously have a mean diameter between 10 and 1000 nm.

The lipid phase of the vesicles, consisting of the lipids and if occasion arises the stabilizer or stabilizers combined therewith, represents advantageously from 0.1 to 16% and preferably from 0.1 to 10% of the total weight of the composition; the ionic and/or non-ionic amphiphilic lipid or lipids represent advantageously from 0.1 to 16% and preferably from 0.1 to 10% of the total weight of the composition; and the stabilizing additive represents advantageously less than 10% of the total weight of the composition.

According to the invention, the melanin pigment is introduced, while stirring, into the dispersion of vesicles already formed.

In the compositions according to the invention, the melanin pigment or pigments, if occasion arises on a filler, are present in proportions in particular between 0.01 and 5% by weight referred to the total weight of the composition.

The vesicles are present in proportions between 0.5 and 15% by weight referred to the total weight of the composition.

The composition according to the invention may be in the form of a more or less thick dispersion, a gel, a cream and a milk.

The composition according to the invention may also include, apart from the melanin pigment or pigments and the vesicles, cosmetically acceptable additives such as dihydroxyacetone, melanin precursors such as tyrosine; silicones, particularly silicone rubbers and mixtures formed from a polydimethylsiloxane hydroxylated at the end of the chain (called dimethiconol according to the nomenclature of the CTFA dictionary) and from a cyclic polydimethylsiloxane (called cyclomethicon according to the nomenclature of the CTFA dictionary), such as the product sold under the name of "Q2-1401" by the company "DOW CORNING;" thickening agents such as crosslinked polyacrylic acids, particularly those sold under the trade names of "CARBOPOL" (for example 934 and 940) by the company "GOODRICH," cellulose derivatives such as more particularly a hydroxyethylcellulose like the one sold under the name of "NATROSOL PLUS GRADE 330 CS" by the company "AQUALON," a xanthan rubber, bentonite, an emulsion of crosslinked ammonium acrylate/acrylamide copolymer sold under the name of "PAS 5161" by the company "HOECHST;" and adjuvants such as mineral and vegetable oils, fatty acid esters, fatty alcohols, ultraviolet filters, mineral pigments such as titanium dioxide, zinc oxide, cerium oxide and ferric oxide, preservatives, perfumes, alkalinizing agents, acidifying agents, stabilizing agents or dyes.

Finally, the invention relates to the use of the composition as defined above for the protection of the skin or hair against ultraviolet radiation and for pigmentation of the skin or hair.

The compositions described above can also be used as a make-up composition (foundations, mascaras, eye shadows, rouges) or for dyeing the hair.

In order to understand the subject of the invention better, several embodiments will now be described as examples purely by way of illustration and without limitation.

EXAMPLE 1

Sun cream

First step: Preparation of an aqueous dispersion of vesicles
  A lipid phase formulated as follows is used:
  Non-ionic amphiphilic lipid of the formula:

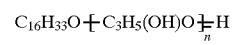

where:
  —$C_3H_5(OH)O$— is represented by the following structures, taken in combination or separately:

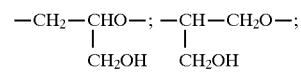

$\overline{n}$ is a mean statistical value equal to 3 . . . 3.8 g

Cholesterol . . . 3.8 g

Dicetylphosphate . . . 0.4 g

The mixture having the above formulation is melted, stirring gently at a temperature of 100°–110° C., and into the melted mixture are progressively introduced 16 g of water brought to 95° C., while stirring slowly, after which it is stirred briskly in a centrifuge provided with blades, until a jellified white broken mass is obtained.

Then 2 g of glycerin and 16.9 g of water are added at 90°–95° C. The temperature and stirring are maintained for 10 minutes.

When the temperature reaches 25° C., the mixture is refined by passing through a high-pressure homogenizer at $5 \times 10^7$ Pa of the "RANNIE" or "GAULIN" type.

Next 2 g of water containing a preservative are introduced, then it is again refined in the high-pressure homogenizer.

The vesicles have a mean diameter of the order of 300 nm.

Second step: Preparation of the cream
  The following ingredients are added to the aqueous dispersion of vesicles obtained in the first step:

Mineral oil . . . 15 g 2-ethylhexyl-p-methoxycinnamate marketed under the name of "PARSOL MCX" by the company "GIVAUDAN" . . . 5 g Melanin pigment obtained by oxidant polymerization of 5,6-dihydroxyindole in the presence of oxygenated water in an ammonia medium . . . 0.1 g Yellow iron oxide . . . 0.04 g Red iron oxide . . . 0.05 g Titanium oxide (anatase) . . . 3 g Crosslinked polyacrylic acid (MW 4,000,000) marketed under the name of "CARBOPOL 940" by the company "GOODRICH" (thickening agent) . . . 0.42 g Triethanolamine . . . 0.4 g Water . . . 30 g Perfume, preservatives . . . sufficient The mineral oil, the 2-ethylhexyl-p-methoxycinnamate and perfume are introduced into the aqueous dispersion of vesicles obtained in the first step, at 35° C., and stirred in a centrifuge. The mixture is refined in a high-pressure homogenizer at 500 bars. Next the melanin pigment is added, then the mixture obtained is passed through a grinder of the "FRYMA" or "DYNOMILL" type. Next the metal oxides are added and it is again passed through the grinder. Lastly the mixture is thickened in a centrifuge with blades, adding to it a highly homogeneous aqueous gel consisting of the thickening agent dissolved with the triethanolamine in the water containing the preservatives and perfume.

The composition obtained in this way is used by topical application at a rate of 2 mg/cm² to an area of skin in a single application. The area of skin treated is subjected to ultra-violet irradiation (OSRAM ULTRAVITALUX lamp) for 10 minutes at a rate of 1 mW/cm². It is found that, one hour after irradiation, no erythema is visible on the area of skin tested, whereas the same irradiation on another area of skin of the same subject leads to erythema in the absence of any prior treatment.

EXAMPLE 2
Tan cream
First step: Preparation of an aqueous dispersion of vesicles
A lipid phase formulated as follows is used:
Non-ionic amphiphilic lipid of the formula:

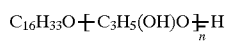

where:
—$C_3H_5(OH)O$— is represented by the following structures, taken in combination or separately:

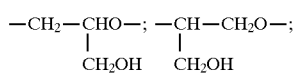

$\overline{n}$ is a mean statistical value equal to 3 . . . 3.8 g
Cholesterol . . . 3.8 g
Monosodium salt of glutamate of the formula:

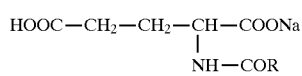

where R is a mixture of $C_{13}$–$C_{21}$ alkyl and/or alkenyl radicals derived from fatty acids of suet, marketed under the name of "ACYLGLUTAMATE HS 11" by the company "AJINOMOTO" . . . 0.4 g The mixture having the above formulation is melted, stirring gently at a temperature of 100°–110° C., and into the melted mixture are progressively introduced 15 g of water brought to 95° C., while stirring slowly, after which it is stirred briskly in a centrifuge provided with blades, until a jellified white broken mass is obtained.

Then 5 g of glycerin and 13 g of water are added at 90°–95° C. The temperature and stirring are maintained for 10 minutes.

Then the temperature is lowered to 60° C. and 5 g of dihydroxyacetone in solution in 3.8 g of water are introduced.

The mixture is refined by passing through a high-pressure homogenizer at 500 bars of the "RANNIE" or "GAULIN" type.

At 40° C., 0.8 g of water containing a preservative are introduced, then it is again refined in the high-pressure homogenizer, The vesicles have a mean diameter of the order of 300 nm.
Second step: Preparation of the cream
The following ingredients are added to the aqueous dispersion of vesicles obtained in the first step:
Mineral oil . . . 12 g
Melanin pigment obtained by oxidant polymerization of 5,6-dihydroxyindole in the presence of oxygenated water in an ammonia medium . . . 0.1 g
Yellow iron oxide . . . 0.15 g
Red iron oxide . . . 0.1 g
Titanium oxide (anatase) . . . 2.2 g
Hydroxyethylcellulose marketed—under the name of "NATROSOL PLUS GRADE 330 CS" by the company "AQUALON" (thickening agent) . . . 0.5 g
Water . . . 30 g
Perfumes, preservative . . . sufficient The mineral oil and perfume are introduced into the aqueous dispersion of vesicles obtained in the first step, at 35° C., and stirred in a centrifuge. The mixture is refined in a high-pressure homogenizer at 500 bars. Next the melanin pigment is added; then the mixture obtained is passed through a grinder of the "FRYMA" or "DYNOMILL" type. Next the metal oxides are added and it is again passed through the grinder. Lastly the mixture is thickened in a centrifuge with blades, adding to it a highly homogeneous aqueous gel consisting of the thickening agent dissolved in the water containing a preservative and perfume.

The composition obtained in this way is used by topical application at a rate of 2 mg/cm² to an area of skin in a single application. After a few hours, the skin colours with a color similar to that of natural tanning.

EXAMPLE 3
Sun lotion
A composition having the following formulation is prepared:
Non-ionic amphiphilic lipid of the formula:

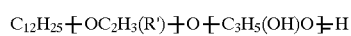

where:
—$C_3H_5(OH)O$— consists of a mixture of the radicals:

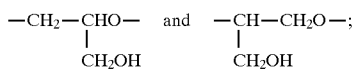

—$OC_2H_3(R')$— consists of a mixture of the radicals:

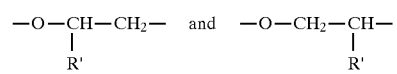

$\overline{n}$ is a mean statistical value equal to 6
R' is a mixture of the radicals $C_{14}H_{29}$ and $C_{16}H_{33}$ . . . 1.9 g
Dimyristylphosphate . . . 0.1 g
Glycerin . . . 1.5 g
Liquid paraffin . . . 15 g
Melanin pigment obtained by oxidant polymerization of 5,6-dihydroxyindole in the presence of oxygenated water in an ammonia medium, on boron nitride marketed under the name of "SH P2" by the company "KAWASAKI" . . . 0.5 g
Mixture of a polydimethylsiloxane hydroxylated at the end of the chain and of octamethylcyclotetrasiloxane (13:87 by weight), marketed under the name of "Q2-1401" by the company "DOW CORNING" . . . 3.4 g
Volatile silicones . . . 1.6 g
2-ethylhexyl monococoate . . . 3 g
Crosslinked polyacrylic acid (MW 4,000,000) marketed under the name of "CARBOPOL 940" by the company "GOODRICH" . . . 0.35 g Triethanolamine . . . 0.33 g Water . . . 76 g Preservatives, perfume . . . sufficient A mixture of the non-ionic lipid and of the dimyristylphosphate is melted, stirring gently at a temperature of 85° C. Into the melted mixture are progressively introduced 4 g of water brought to 85° C., while stirring slowly, after which it is stirred briskly in a centrifuge provided with blades, until a jellified white broken mass is obtained.

Then the glycerin and 42 g of water are added at 60° C. while stirring rapidly. The temperature and stirring are maintained for 10 minutes. Then the liquid paraffin preheated to 60° C. is added.

When the temperature reaches 25° C., the mixture is refined by passing it twice through a high-pressure homogenizer at 500 bars of the "RANNIE" or "GAULIN" type.

Next the melanin pigment on boron nitride is added, then stirred for 5 minutes. Then the mixture of polysiloxanes, the volatile silicones and the 2-ethylhexyl monococoate are added. Next it is stirred for 10 minutes.

Lastly the mixture is thickened in a centrifuge with blades, while adding to it a highly homogeneous aqueous gel consisting of the thickening agent dissolved with the triethanolamine in 30 g of water containing preservatives and perfume.

The composition obtained in this way is used as in example 1. The same results are observed.

EXAMPLE 4

After-sun cream

A composition is prepared according to the following formulation:

Non-ionic lipid of the formula:

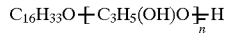

where:
—$C_3H_5(OH)O$— is represented by the following structures, taken in combination or separately:

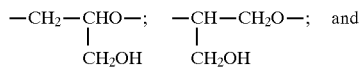

$\overline{n}$ is a mean statistical value equal to 3 . . . 3.8 g

Cholesterol . . . 3.8 g

Dicetylphosphate . . . 0.4 g

Glycerin . . . 2 g

Liquid paraffin . . . 15 g

Melanin pigment obtained by oxidant polymerization of 5,6-dihydroxyindole in the presence of oxygenated water in an ammonia medium, on bismuth oxychloride marketed under the name of "PEARL GLO UVR 1086" by the company "MALLINCKRODT" . . . 0.5 g Terpene derivative (bisabolol) marketed under the name of "DRAGOSANTOL" by the company "DRAGOCO" . . . 0.5 g Crosslinked polyacrylic acid (MW 4,000,000) marketed under the name of "CARBOPOL 940" by the company "GOODRICH" . . . 0.42 g Triethanolamine . . . 0.4 g Water . . . 88 g Preservative, perfume . . . sufficient A mixture of the non-ionic lipid, the cholesterol and the dicetylphosphate is melted, stirring gently at a temperature of 100°–110° C. Into the melted mixture are progressively introduced 16 g of water brought to 95° C., while stirring slowly, after which it is stirred briskly in a centrifuge provided with blades, until a jellified white broken mass is obtained.

Then the glycerin and 42 g of water are added at 60° C. The temperature and stirring are maintained for 10 minutes. Then the liquid paraffin is added.

The mixture is refined by passing it twice through a high-pressure homogenizer at 500 bars of the "RANNIE" or "GAULIN" type.

Next the melanin pigment on bismuth oxychloride is added, and stirred for 5 minutes. Then the terpene derivative is added.

Lastly the mixture is thickened in a centrifuge with blades, adding to it a highly homogeneous aqueous gel consisting of the thickening agent dissolved in 30 g of water containing a preservative and perfume, and neutralised by the triethanolamine.

The composition obtained in this way is used by topical application at a rate of 2 mg/cm² to an area of skin previously exposed to the sun. Apart from its soothing function, this cream confers a slight tanning of the skin.

EXAMPLE 5

Sun cream

The following formulation is prepared:

Non-ionic lipid of the formula:

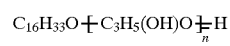

where:
—$C_3H_5(OH)O$— is represented by the following structures, taken in combination or separately:

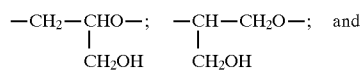

$\overline{n}$ is a mean statistical value equal to 3 . . . 3.8 g

Cholesterol . . . 3.8 g

Dicetylphosphate . . . 0.4 g

Glycerin . . . 2 g

Liquid paraffin . . . 14.4 g

Melanin pigment obtained by oxidant polymerization of 5,6-dihydroxyindole in the presence of oxygenated water in an ammonia medium on mica marketed under the name of "MICA CONCORD 1000" by the company "SCIAMA" . . . 0.5 g Yellow iron oxide . . . 0.04 g Sienna iron oxide . . . 0.05 g Crosslinked polyacrylic acid (MW 4,000,000) marketed under the name of "CARBOPOL 940" by the company "GOODRICH" . . . 0.42 g Triethanolamine . . . 0.4 g Water . . . 74 g Preservative, perfume . . . sufficient A mixture of the non-ionic lipid, the cholesterol and the dicetylphosphate is melted, stirring gently at a temperature of 100°–110° C. Into the melted mixture are progressively introduced 16 g of water brought to 85° C., while stirring slowly, after which it is stirred briskly in a centrifuge provided with blades, until a jellified white broken mass is obtained.

Then the glycerin and 28 g of water are added at 60° C. The temperature and stirring are maintained for 10 minutes. Then the liquid paraffin preheated to 60° C. is added.

The mixture is refined by passing it twice through a high-pressure homogenizer at 500 bars of the "RANNIE" or "GAULIN" type.

Next the melanin pigment on mica is added while stirring, then the iron oxides are added while stirring.

Lastly the mixture is thickened in a centrifuge with blades, adding to it a highly homogeneous aqueous gel consisting of the thickening agent dissolved in 30 g of water containing a preservative and perfume, and neutralized by the triethanolamine.

The composition obtained in this way is used by the method described in example 1. The same results are observed.

EXAMPLE 6

Anti-sun cream

An anti-sun cream is prepared in the following manner:

In a first step 3.2 g of polyoxyethylenated phytosterol with 5 moles of ethylene oxide sold by the company NIKKO under the trade name "GENEROL 122 E5" are melted, while stirring gently, at a temperature of 85° C. Then 4.8 g of hydrogenated lecithin with 30–35% of hydrogenated phosphatidyl choline sold by the company NIKKO under the trade name "LECINOL S10" are added to the melted mixture, this being until complete homogenization (5 minutes).

24 g of water brought to 80° C. and containing a preservative are introduced into the melted mixture, and it is mixed for about 5 minutes; then the mixture is allowed to swell for 1 hour. 36 g of water are added to the phase obtained in this way, at 20° C.; the mixture is stirred for a few minutes, and the mixture is refined by passing it through a high-pressure homogenizer at 5×10$^7$ Pa of the "RANNIE" or "GAULIN" type before letting the mixture return to ambient temperature.

In a second step, a mixture of 0.5 g of melanin pigment obtained by oxidation of 5,6-dihydroxyindole and 10 g of liquid paraffin is added while stirring with the "ULTRA TURRAX."

A highly homogeneous aqueous gel consisting of 0.4 g of thickening agent sold under the trade name "CARBOPOL 940" by the company GOODRICH dissolved in 8 g of water containing a preservative, is prepared. To this gel are added 10 g of cerium oxide sold under the trade name "OPALINE BROYEE" by the company RHONE POULENC. Next this gel is added to the dispersion of vesicles, then it is made up to 100 g with water. The pH is adjusted to 6.5 with triethanolamine.

The composition obtained in this way is used by the method described in example 1. The same results are observed.

EXAMPLE 7

Skin protection cream

A skin protection cream is prepared in the following manner:

In a first step a mixture of 3.8 g of non-ionic lipid of the formula:

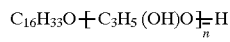

in which formula:

$\overline{n}$ is a mean statistical value equal to 3 and
—C$_3$H$_5$ (OH)O— is represented by the following structures taken in combination or separately:

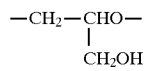

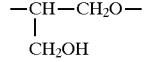

with 3.8 g of cholesterol and 0.4 g of dicetylphosphate is melted while stirring gently at a temperature of 100°–110° C.

16 g of water brought to 85° C. and containing a preservative are introduced progressively into the melted mixture, and it is mixed for about 5 minutes. 24 g of water are added to the phase obtained in this way, at 20° C. The mixture is stirred for a few minutes.

The mixture is refined by passing it twice through a high-pressure homogenizer at 5×10$^7$ Pa of the "RANNIE" or "GAULIN" type.

Next a mixture of 0.002 g of cuttlefish melanin and 15 g of liquid paraffin is added. Then it is stirred for 5 minutes.

A highly homogeneous aqueous gel consisting of 0.42 g of thickening agent sold under the trade name "CARBOPOL 940" by the company GOODRICH, dissolved in 30 g of water containing a preservative, is prepared. To this gel are added 2 g of titanium oxide sold under the trade name "P 25" by the company DEGUSSA. Next this gel is added to the dispersion of vesicles, then it is made up to 100 g with water. The pH is adjusted to 7 with triethanolamine.

The composition obtained in this way is used by topical application. It confers on the skin great softness and a slight tan.

EXAMPLE 8 (Comparative)

Two types of composition were prepared by way of comparison.

Composition A$_1$ (not forming part of the invention)

Composition A$_1$ was prepared by the method described in example 2 of EP-A-0 386 380 so as to contain melanin inside the vesicles by adding melanin before formation of the vesicles.

Composition A$_1$ has the following formulation (by weight):

Lipid phase . . . 8 % consisting of:
  α-phosphatidyl choline . . . 6.26 %
  Dicetylphosphate . . . 1.29 %
  Cholesterol . . . 0.45 %
"SIGMA" synthetic melanin obtained by oxidation of tyrosine with the aid of a persulphate having a granulometry less than 1 μm . . . 0.1 %
Thickening agent sold under the trade name "CARBOPOL 940" by the company GOODRICH . . . 0.3 %
Water . . . quantity sufficient for 100 %

Composition A$_2$

This composition is identical with composition A$_1$, except that it contains no melanin.

Composition B$_1$ (according to the invention)

Composition B$_1$ was prepared as described in example 1, adding melanin after formation of the vesicles to the outer phase of the dispersion of the vesicles.

Composition B$_1$ has the following formulation (by weight):

Lipid phase . . . 8 % consisting of:

Non-ionic amphiphilic lipid . . . 6.26 % of the formula:

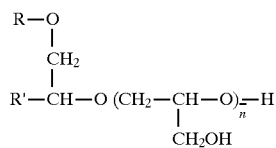

where:
R is the radical $C_{12}H_{25}$
R' is a mixture of radicals $C_{14}H_{29}$ and $C_{16}H_{33}$
$\overline{n}$ is a statistical value equal to 6
Monosodium salt of glutamate sold under the trade name "ACYLGLUTAMATE HS 11" by the company AJINOMOTO . . . 0.8 %
Melanin pigment obtained by oxidant polymerization of 5,6-dihydroxyindole in the presence of oxygenated water in an ammonia medium having a granulometry of 15 μm . . . 0.1 %
Thickening agent sold under the trade name "CARBOPOL 940" by the company GOODRICH . . . 0.3 %
Water . . . quantity sufficient for 100 %
Composition $B_2$ is identical with composition $B_1$ except that it contains no melanin.

Tests

Compositions $A_1$, $A_2$, $B_1$ and $B_2$ were mixed with 10% by weight of linoleic acid, and the mixtures obtained were subjected to the sun test for 7 hours. Absorption was measured with a spectrophotometer at 233 nm (which depends on the quantity of diene hydroperoxides present at time $T_0$ before the sun test and at time $T_7$ after the sun test); the results obtained are given in the table below:

| Product | $T_0$ | $T_7$ | Difference $T_7$–$T_0$ |
|---|---|---|---|
| $A_2$ | 0.84 | 1.21 | 0.37 |
| $A_1$ | 1.55 | 1.69 | 0.14 |
| $B_2$ | 1.16 | 1.24 | 0.08 |
| $B_1$ | 0.97 | 0.95 | 0.02 |

These results show that composition $B_1$ according to the invention inhibits peroxidation of unsaturated fats.

EXAMPLE 9

Epidermis protecting foundation

Operating as in example 5, a composition having the following formulation is prepared:

Polyglycerolated cetyl alcohol . . . 2.7 g with 3 moles of glycerol
Cholesterol . . . 2.7 g
Glycerin . . . 2 g
Monomethylsilanol lactate in water at 1% . . . 5 g
Isoparaffin . . . 8 g
Cyclopentadimethylsiloxane . . . 6 g
Sesame seed oil . . . 8 g
Liquid fraction of karite butter . . . 2 g
Mixture of palmitoyl collagenic acid of . . . 0.6 g Bovidae, palmitic acid, isopropyl palmitate (60/20/12 by weight)
Melanin pigment obtained by oxidant polymerization of 5,6-dihydroxyindole in the presence of oxygenated water in an ammonia medium (granulometry: 15μ) . . . 0.1 g
Yellow iron oxide . . . 0.5 g
Brown and yellow iron oxide . . . 0.32 g
Black iron oxide . . . 0.15 g
Titanium oxide . . . 3.03 g
2-ethylhexyl paramethoxycinnamate . . . 1 g
Triethanolamine . . . 0.5 g
Carboxyvinyl polymer synthesised in . . . 0.5 g ethyl acetate
Sterilized demineralized water . . . 62.3 g The composition obtained in this way is applied to the skin of the face. It confers on the skin great softness and a slightly tanned appearance.

I claim:

1. A cosmetic composition in the form of an aqueous dispersion of vesicles having a lamellar structure and encapsulating an aqueous phase, said aqueous dispersion also containing, dispersed therein, at least one melanin pigment, the lipid phase of said vesicles being present in an amount ranging from 0.1 to 16 percent by weight based on the total weight of said composition, said melanin pigment being present in an amount ranging from 0.01 to 5 percent by weight based on the total weight of said composition, said vesicles having a diameter between 10 and 1,000 nm and said melanin pigment having a particle size between about 500 nm and 50,000 nm.

2. The composition of claim 1 wherein at least one melanin pigment is obtained by oxidation of at least one indole compound, or by extraction of melanin from a substance containing melanin.

3. The composition of claim 2 wherein said indole compound has the formula:

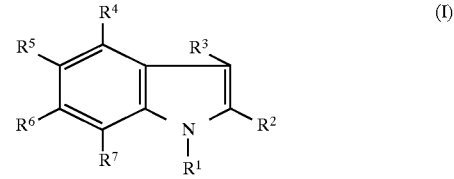

wherein
$R^1$ and $R^3$, each independently, represent hydrogen or $C_1$–$C_4$ alkyl;
$R^2$ represents hydrogen, $C_1$–$C_4$ alkyl, carboxyl or ($C_1$–$C_4$) alkoxy carbonyl;
$R^4$ and $R^7$, each independently, represent hydrogen, hydroxy, $C_1$–$C_4$ alkyl, amino, $C_1$–$C_4$ alkoxy, ($C_2$–$C_4$ acyl) oxy or ($C_2$–$C_4$ acyl) amino;
$R^5$ represents hydrogen, hydroxy, $C_1$–$C_4$ alkoxy, $C_1$–$C_4$ alkyl, halogen, amino, ($C_2$–$C_{14}$ acyl) oxy, ($C_2$–$C_4$ acyl) amino or trimethylsilyloxy;
$R^6$ represents hydrogen, hydroxy, $C_1$–$C_4$ alkoxy, amino, ($C_2$–$C_4$ acyl) oxy, ($C_2$–$C_4$ acyl) amino, trimethylsilyloxy or ($C_2$–$C_4$ hydroxyalkyl) amino; or
$R^5$ and $R^6$ together with the carbon atoms to which they are attached form a methylenedioxy ring optionally substituted by a $C_1$–$C_4$ alkyl group, a $C_1$–$C_4$ alkoxy group or a carbonyldioxy ring;
at least one of $R^4$ to $R^7$ represents OZ or $NHR^0$ with not more than one of said $R^4$ to $R^7$ representing $NHR^0$ and not more than two of said $R^4$ to $R^7$ representing OZ, and when Z represents hydrogen the resulting two OH groups are in positions 5 and 6; and at least one of $R^4$ to $R^7$ represents hydrogen, and when only one of $R^4$ to $R^7$ represents hydrogen, only one of $R^4$ to $R^7$ represents $NHR^0$ or OZ, the remainder representing $C_1$–$C_4$ alkyl;
$R^0$ represents hydrogen, $C_2$–$C_4$ acyl, or $C_2$–$C_4$ hydroxyalkyl and Z represents hydrogen, $C_2$–$C_{14}$ acyl, $C_1$–$C_4$ alkyl or trimethylsilyl, and
an alkali metal, alkaline earth metal, ammonium or amine salt thereof.

4. The composition of claim 3 wherein said indole compound is selected from the group consisting of:
4-hydroxyindole,
5-hydroxyindole,
6-hydroxyindole,
7-hydroxyindole,
4-hydroxy-5-methoxyindole,
4-hydroxy-5-ethoxyindole,
2-carboxyl-5-hydroxyindole,
5-hydroxy-6-methoxyindole,
6-hydroxy-7-methoxyindole,
5-methoxy-6-hydroxyindole,
5,6-dihydroxyindole,
N-methyl-5,6-dihydroxyindole,
2-methyl-5,6-dihydroxyindole,
3-methyl-5,6-dihydroxyindole,
2,3-dimethyl-5,6-dihydroxyindole,
2-carboxyl-5,6-dihydroxyindole,
4-hydroxy-5-methylindole,
2-carboxyl-6-hydroxyindole,
6-hydroxy-N-methylindole,
2-ethoxycarbonyl-5,6-dihydroxyindole,
4-hydroxy-7-methoxy-2,3-dimethylindole,
4-hydroxy-5-ethoxy-N-methylindole,
6-hydroxy-5-methoxy-2-methylindole,
6-hydroxy-5-methoxy-2,3-dimethylindole,
6-hydroxy-2-ethoxycarbonylindole,
7-hydroxy-3-methylindole,
5-hydroxy-6-methoxy-2,3-dimethylindole,
5-hydroxy-3-methylindole,
5-acetoxy-6-hydroxyindole,
5-hydroxy-2-ethoxycarbonylindole,
6-hydroxy-2-carboxy-5-methylindole,
6-hydroxy-2-ethoxycarbonyl-5-methoxyindole,
6-N-B-hydroxyethylaminoindole,
4-aminoindole,
5-aminoindole,
6-aminoindole,
7-aminoindole,
N-methyl-6B-hydroxyethylaminoindole,
6-amino-2,3-dimethylindole,
6-amino-2,3,4,5-tetramethylindole,
6-amino-2,3,4-trimethylindole,
6-amino-2,3,5-trimethylindole,
6-amino-2,3,6-trimethylindole,
5,6-diacetoxyindole,
5-methoxy-6-acetoxyindole,
5,6-dimethoxyindole,
5,6-dibenzyloxyindole,
5,6-methylenedioxyindole,
5,6-trimethylsilylindole,
5,6-dihydroxyindole phosphoric ester and
an acid addition salt thereof.

5. The composition of claim 1 wherein said at least one melanin pigment is combined with at least one particulate filler.

6. The composition of claim 5 wherein said particulate filler is an inert mineral filler having a granulometry less than 20,000 nm.

7. The composition of claim 5 wherein said particulate filler is an inert polymeric filler having a granulometry less than 100,000 nm and being a natural or synthetic, organic or inorganic, crosslinked, crystalline or amorphous polymer.

8. The composition of claim 7 wherein said polymer is derived from keratin, chitin, cellulose or a polyamide; or a homopolymer or copolymer resulting from the polymerization of a monoethylenic or polyethylenic, aliphatic or aromatic, crosslinked, crystalline or amorphous monomer.

9. The composition of claim 8 wherein said polymer derived from keratin is a polymer derived from an animal or a human keratin, a chemically modified keratin, a partially hydrolyzed keratin; a sulphonic keratin; or a silk fibroin.

10. The composition of claim 8 wherein said polymer derived from chitin is a polymer derived from chitin, a deacetylated chitin or a mixture thereof.

11. The composition of claim 8 wherein said polymer derived from cellulose is a microcrystalline cellulose.

12. The composition of claim 8 wherein said polymer is selected from the group consisting of polyethylene, polypropylene, polystyrene, poly(methyl methacrylate) and crosslinked poly (methyl methacrylate).

13. The composition of claim 8 wherein said polymer is crosslinked poly-β-alanine.

14. The composition of claim 7 wherein said polymeric filler is hollow microspheres of a vinylidene chloride and acrylonitrile copolymer or porous microspheres of polyamide 12, polyamide 6 or copolyamide 6/12.

15. The composition of claim 7 wherein said polymeric filler is microsponges of a crosslinked styrene/divinylbenzene polymer, a crosslinked methyl methacrylate/ethylene glycol dimethacrylate polymer or a crosslinked vinyl stearate/divinylbenzene polymer.

16. The composition of claim 7 wherein said polymeric filler is a silicone polymer.

17. The composition of claim 5 wherein said particulate filler is a filler consisting of organic or mineral particles with a lamellar structure having a size less than 50,000 nm.

18. The composition of claim 17 wherein said particles with a lamellar structure are selected from the group consisting of L-lauroyllysine, ceramic micro particles optionally coated with zirconium powder, lamellar titanium dioxide, lamellar talc, boron nitride, lamellar mica and bismuth oxychloride.

19. The composition of claim 17 wherein said particles with a lamellar structure consist of layers for which the ratio between the largest dimension and the thickness is between 2 and 100.

20. The composition of claim 1 wherein said lipid phase of said vesicles is selected from the group consisting of a nonionic amphiphilic lipid, an ionic amphiphilic lipid and a mixture thereof.

21. The composition of claim 20 wherein said nonionic amphiphilic lipid is selected from the group consisting of:
(1) a linear or branched polyglycerol ether having the formula:

wherein
—$C_3H_5(OH)O$— represents the following structures, taken in combination or separately:

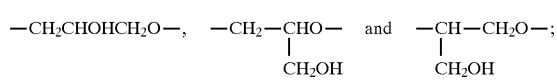

$\bar{n}$ is a mean statistical average value between 2 and 6;
$R^{10}$ represents
   (a) an aliphatic, linear or branched chain radical containing 12 to 18 carbon atoms,
   (b) R"CO wherein R" represents an aliphatic, linear or branched $C_{11}$–$C_{17}$ radical, or

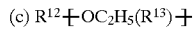

wherein $R^{12}$ has the meaning (a) or (b) given above, —$OC_2H_5$ represents the following structures, taken in combination or separately:

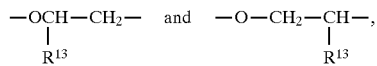

and $R^{13}$ has the meaning (a) given above;
(2) a polyoxyethylenated fatty alcohol;
(3) a polyhydric alcohol ester optionally polyoxyethylenated;
(4) a cerebroside; and
(5) an oxyethylenated polyglycerol stearate.

22. The composition of claim 20 wherein said lipid phase also contains at least one stabilizing additive selected from the group consisting of a sterol and an anionic stabilizer.

23. The composition of claim 20 wherein said vesicles have a mean diameter ranging from 10 to 1,000 nm.

24. The composition of claim 1 wherein said vesicles are present in an amount ranging from 0.5 to 15 percent by weight based on the total weight of said composition.

25. The composition of claim 1 in the form of a lotion, a gel, a cream or a milk.

26. The composition of claim 1 which also contains at least one cosmetically acceptable additive selected from the group consisting of dihydroxyacetone, a silicone, a thickening agent, a mineral oil, a vegetable oil, a fatty acid ester, a fatty alcohol, an ultraviolet filter, a mineral pigment, a preservative, a perfume, an alkalinizing agent, an acidifying agent, a stabilizing agent and a dye.

27. A method for protecting the skin or hair against ultraviolet radiation comprising applying to said skin or hair the composition of claim 1 in an amount effective to protect said hair or skin against ultraviolet radiation.

28. A method for making up the skin comprising applying to the skin the composition of claim 1 in an amount effective to make up the skin.

29. A method for dyeing the hair comprising applying to the hair the composition of claim 1 in an amount effective to dye said hair.

* * * * *